US012394066B2

(12) United States Patent
Blaga et al.

(10) Patent No.: US 12,394,066 B2
(45) Date of Patent: Aug. 19, 2025

(54) METHOD AND SYSTEM FOR DETECTING LIVESTOCK RESPIRATORY COMPROMISE

(71) Applicant: The Main Branch, Inc., Woodinville, WA (US)

(72) Inventors: Octavian Alexandru Blaga, Chattanooga, TN (US); David Benjamin Scott, Woodinville, WA (US)

(73) Assignee: Synetic, Inc., Woodinville, WA (US)

( * ) Notice: Subject to any disclaimer, the term of this patent is extended or adjusted under 35 U.S.C. 154(b) by 76 days.

(21) Appl. No.: 18/537,876

(22) Filed: Dec. 13, 2023

(65) Prior Publication Data

US 2024/0196865 A1 Jun. 20, 2024

Related U.S. Application Data

(60) Provisional application No. 63/387,491, filed on Dec. 14, 2022, provisional application No. 63/387,488, filed on Dec. 14, 2022, provisional application No. 63/387,490, filed on Dec. 14, 2022.

(51) Int. Cl.

| | |
|---|---|
| *G06T 7/246* | (2017.01) |
| *A01K 11/00* | (2006.01) |
| *A01K 29/00* | (2006.01) |
| *A61B 5/00* | (2006.01) |
| *A61B 5/024* | (2006.01) |
| *G06T 5/70* | (2024.01) |
| *G06T 7/00* | (2017.01) |
| *G06T 7/277* | (2017.01) |
| *G06T 7/73* | (2017.01) |
| *G06V 10/26* | (2022.01) |
| *G06V 10/30* | (2022.01) |
| *G06V 10/44* | (2022.01) |
| *G06V 10/75* | (2022.01) |

(Continued)

(52) U.S. Cl.
CPC ............ *G06T 7/246* (2017.01); *A01K 11/006* (2013.01); *A01K 29/005* (2013.01); *A61B 5/02416* (2013.01); *A61B 5/742* (2013.01); *G06T 5/70* (2024.01); *G06T 7/0012* (2013.01); *G06T 7/277* (2017.01); *G06T 7/73* (2017.01); *G06V 10/26* (2022.01); *G06V 10/30* (2022.01); *G06V 10/44* (2022.01); *G06V 10/751* (2022.01); *G06V 10/764* (2022.01); *G06V 40/10* (2022.01); *A61B 2503/40* (2013.01); *G06T 2207/10016* (2013.01); *G06T 2207/20221* (2013.01); *G06T 2207/30004* (2013.01); *G06T 2207/30232* (2013.01)

(58) Field of Classification Search
None
See application file for complete search history.

(56) References Cited

U.S. PATENT DOCUMENTS

| | | | |
|---|---|---|---|
| 10,292,369 B1 * | 5/2019 | Heath | A61B 5/0205 |
| 2014/0236036 A1 * | 8/2014 | de Haan | A61B 5/1128 |
| | | | 600/534 |
| 2018/0333244 A1 * | 11/2018 | Hanks | A61B 5/7278 |

* cited by examiner

*Primary Examiner* — Thomas S McCormack
(74) *Attorney, Agent, or Firm* — PatentVest, Inc.; Matthew L. Bycer

(57) ABSTRACT

Video cameras capture video images of livestock and transmit the images to a computer. The computer identifies individual livestock based on biometric markings. The computer performs pixel enhancement to amplify breathing motion and calculates a respiration rate. A sudden increase in respiration rate indicates respiratory compromise, such as pneumonia or BRD.

13 Claims, 9 Drawing Sheets

(51) Int. Cl.
*G06V 10/764* (2022.01)
*G06V 40/10* (2022.01)

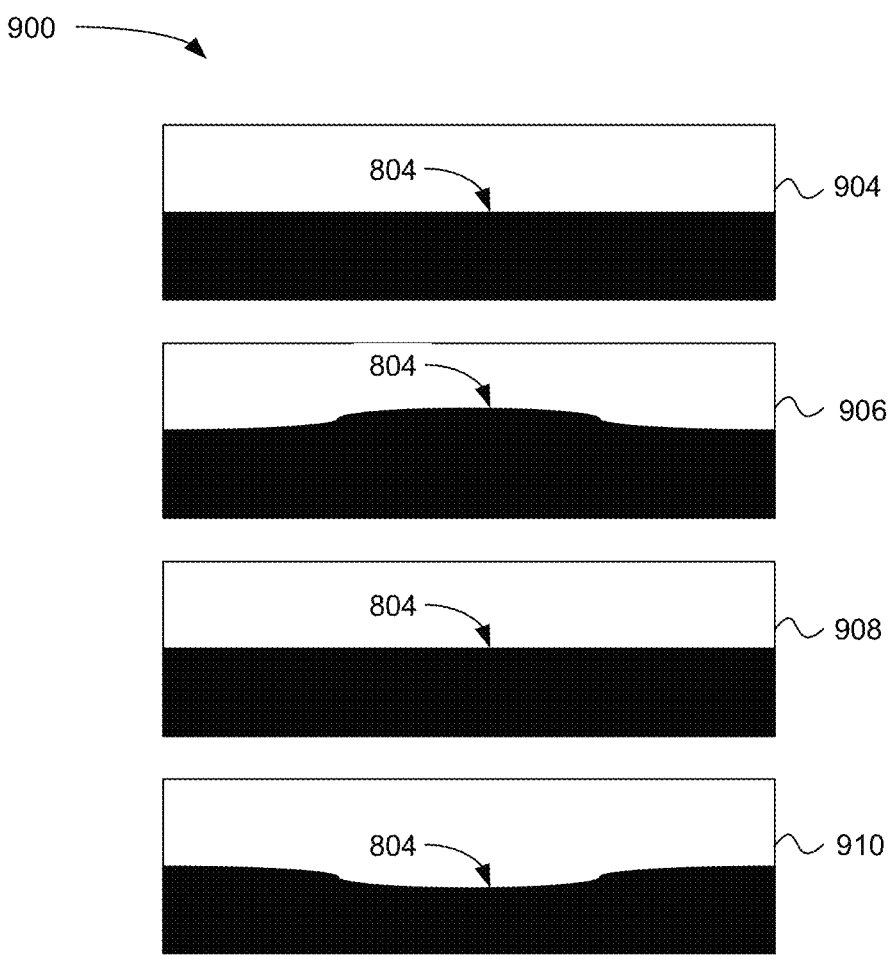

METHOD AND SYSTEM FOR DETECTING LIVESTOCK RESPIRATORY COMPROMISE

CROSS REFERENCE TO RELATED APPLICATIONS

The present application claims benefit of U.S. Provisional Patent Application No. 63/387,491, entitled "METHOD AND SYSTEM FOR DETECTING LIVESTOCK RESPIRATORY COMPROMISE", filed Dec. 14, 2022; U.S. Provisional Patent Application No. 63/387,488, entitled "LIVESTOCK HEART RATE MONITORING", filed Dec. 14, 2022 and U.S. Provisional Patent Application 63/387,490, entitled "COMPUTER METHOD AND APPARATUS FOR TAGLESS TRACKING OF LIVESTOCK", filed Dec. 14, 2022.

The foregoing applications, to the extent not inconsistent with the disclosure herein, are incorporated by reference.

SUMMARY

According to an embodiment, a computer method for measuring respiration rate in livestock includes receiving a video stream including images of one or more livestock; determining, from the video stream images, a digital identity of a livestock individual; finding, in frames of the video stream, a feature of the livestock individual that exhibits respiration rate-correlated periodic movement; performing pixel amplification at the feature to amplify the periodic movement; and calculating a respiration rate of the livestock individual from a sequence of the amplified periodic movement. The computer method may further include outputting information about the respiration rate of the livestock individual on an electronic display.

BRIEF DESCRIPTION OF THE DRAWINGS

FIG. 9 is a diagram showing a sequence of video frames exhibiting pixel-amplified periodic movement at the feature of the livestock, according to an embodiment.

DETAILED DESCRIPTION

Figure 1:
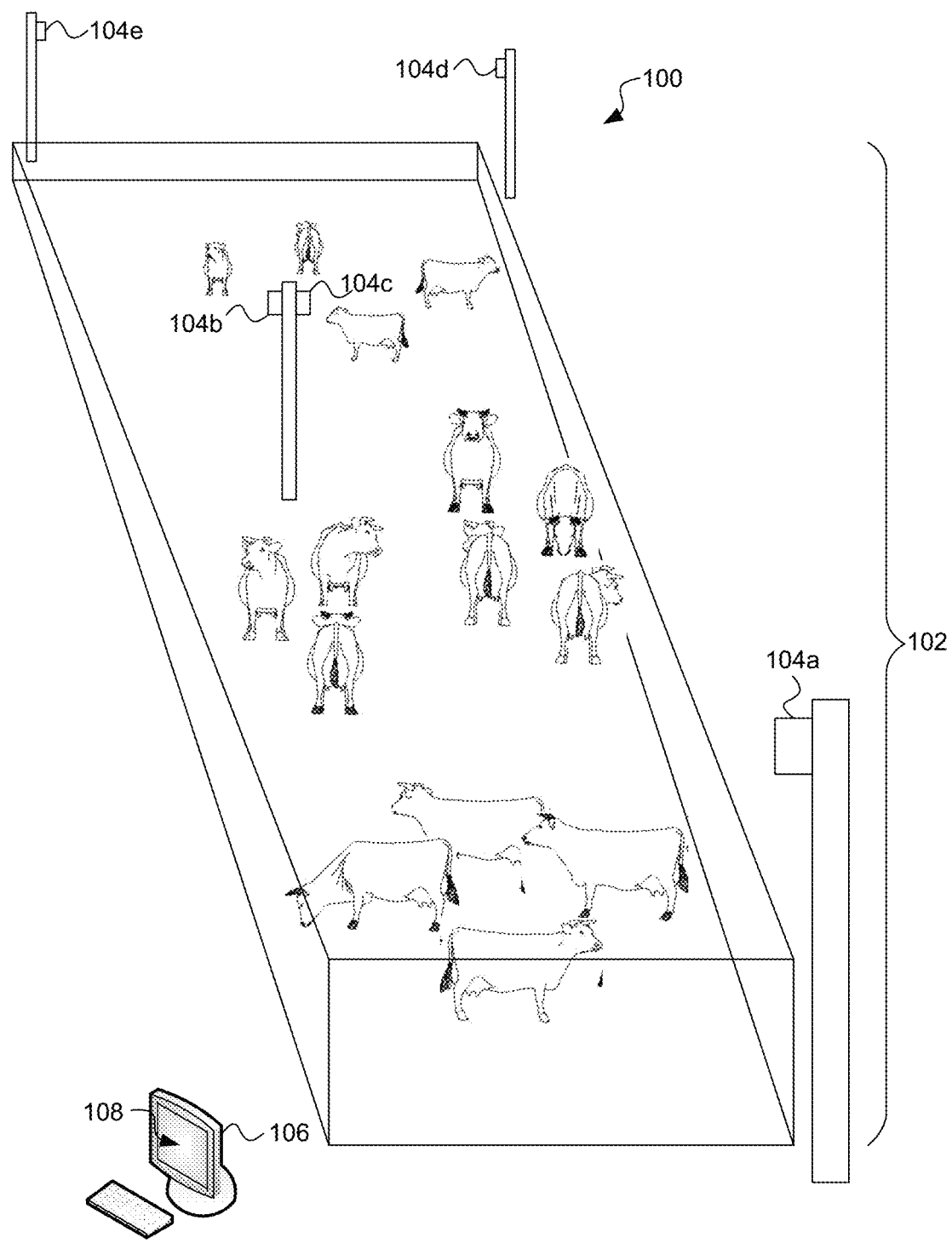
FIG. 1 is a diagram of a system for monitoring livestock health, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1 is a diagram of a system 100 for monitoring livestock health, according to an embodiment. A plurality of livestock 102 may be constrained by a peripheral fence, for example in a feedlot. The computer methods described herein may be performed on such a peripherally constrained plurality of livestock, or may be performed on livestock with no nearby constraint.

A plurality of sensors 104, here shown as cameras 104a, 104b, 104c, 104d, 104e, are disposed to obtain digital video or sequences of still frames including the livestock 102. The digital video or sequences of still frames are transmitted to a computer 106. The computer 106 may process the digital video or sequences of still frames as described below. The computer 106 may display the videos or sequences of still frames on an electronic display 108 for viewing by a user. Additionally or alternatively the computer 106 may display other indicia, optionally overlaying the fields of view, derived from processing described below.

Figure 2:
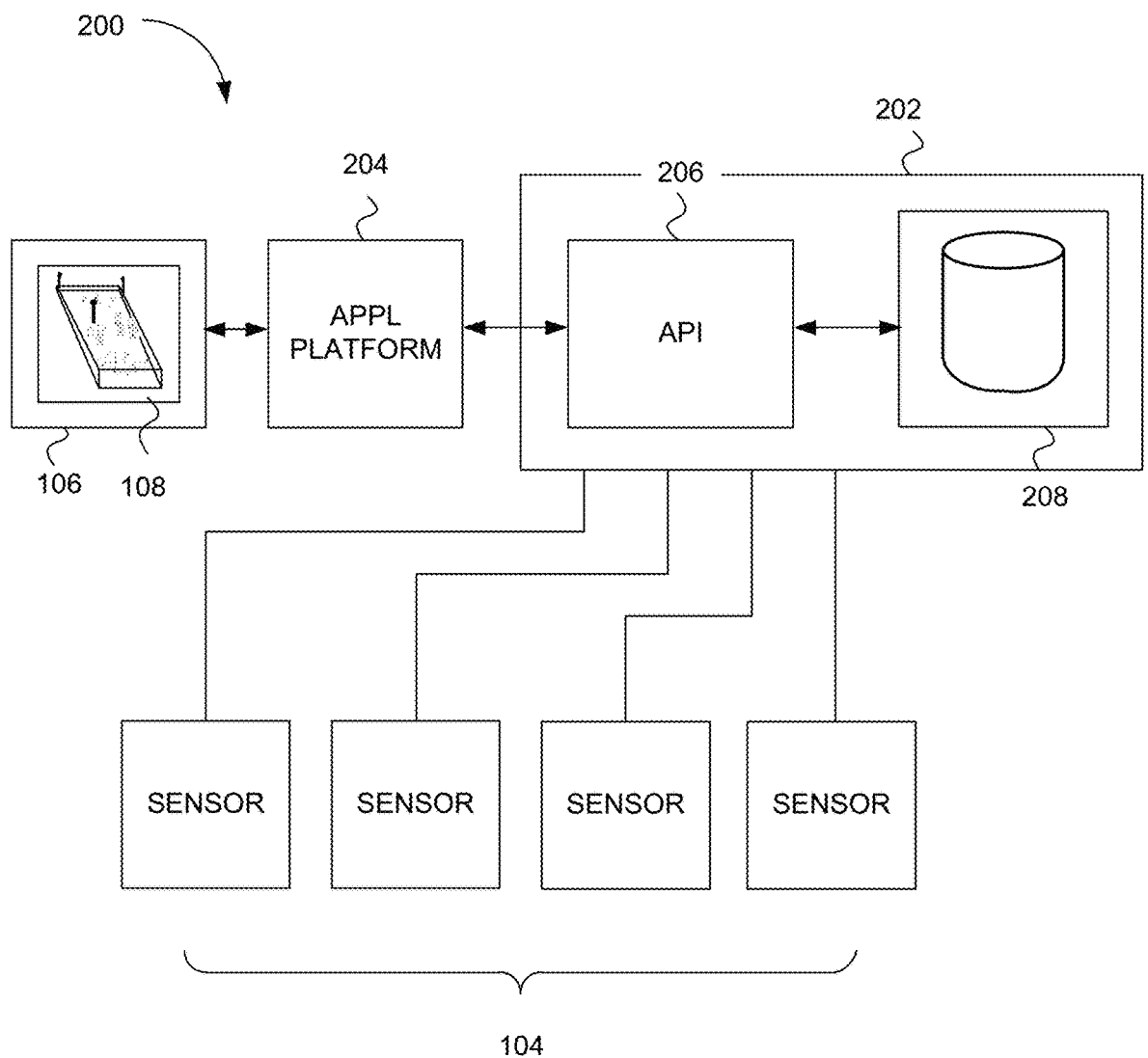
FIG. 2 is a block diagram of a computer system for tagless tracking and biometric identification of livestock, according to an embodiment.

FIG. 2 is a block diagram of a computer system for tag-less tracking and biometric identification of livestock, according to an embodiment. The cameras 104a, 104b, 104c, 104d, 104e are indicated as sensors 104. The sensors 104 may optionally include other sensing modalities in addition to focal plane imaging. Optionally, the sensors 104 are configure to provide hyper-spectral imaging. The sensors are operatively coupled to a computer 202. As shown in FIG. 2, the computer 106 shown in FIG. 1 may be configured as a client or peer device. Optionally all processing described herein may be performed in a single computer 106. The computer 106 may include a thin client, a portable or non-portable computer, a personal electronic device such as a smart phone, or other platform capable of receiving data and driving an electronic display 108.

The computer 202 may be a server computer, and/or may include a server farm, a set of pipelined servers, relay servers, etc. as is known in the art of computer networking. The server 202 may receive data from the sensors 104 and process the data as describe herein. The server may include an application program interface (API) portion 206 operatively coupled to an application platform 204. The application platform 204 may be included in the server 202, may be included in the local computer 106, or may be otherwise operatively coupled therebetween. The server 202 (and/or computer 106) include a non-transitory computer readable memory 208 such as a rotating disk or solid state memory. The non-transitory computer readable memory may support a database, look-up table, or other software structure to enable storage and retrieval of information described below. Typically, the computer 202 includes a microprocessor, memory, and other components appropriate for performing image processing on the data received from the sensors 104.

Figure 3:
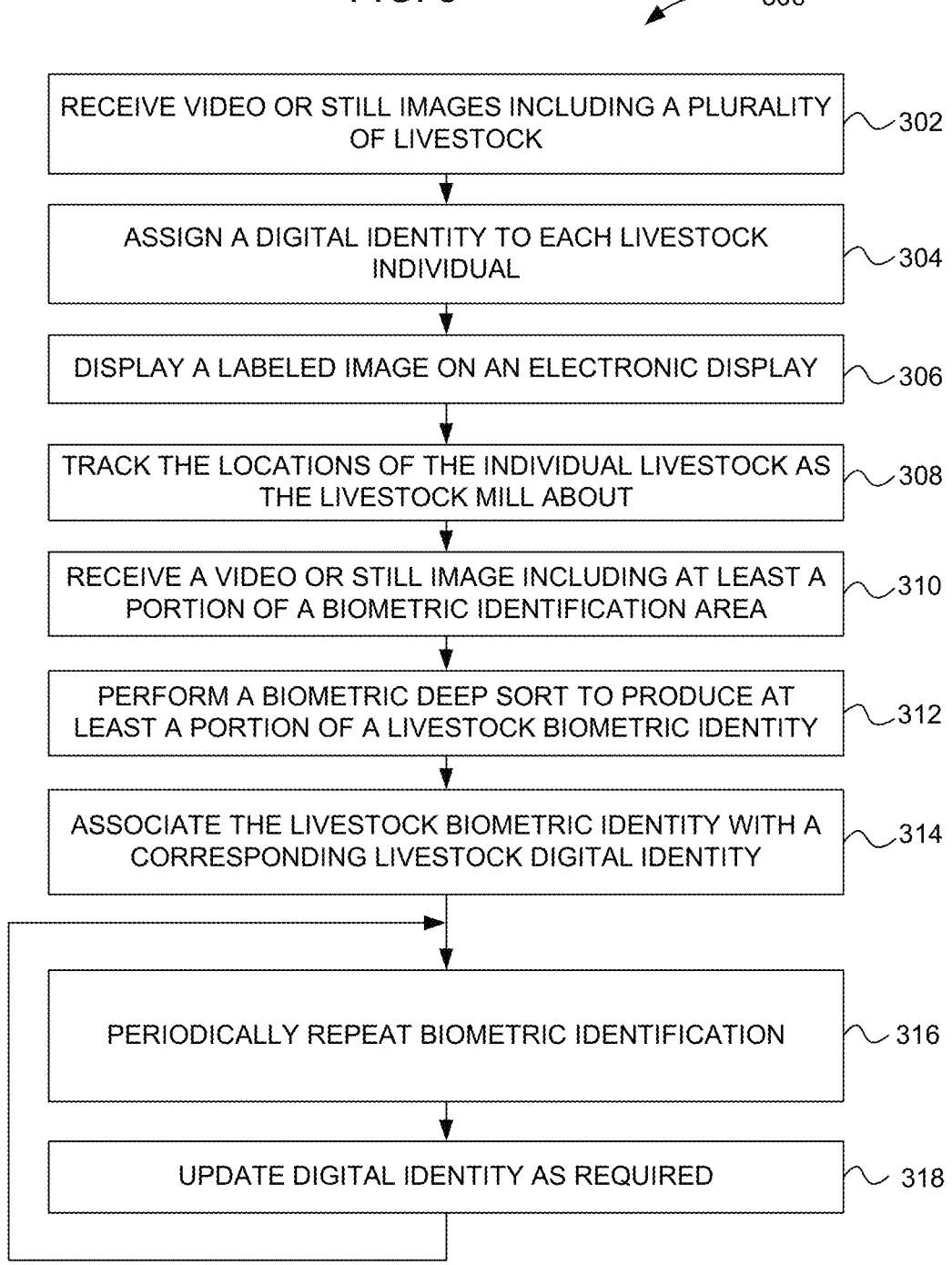
FIG. 3 is a flowchart showing a computer method for livestock biometric identification and tracking, according to an embodiment.
Figure 5:
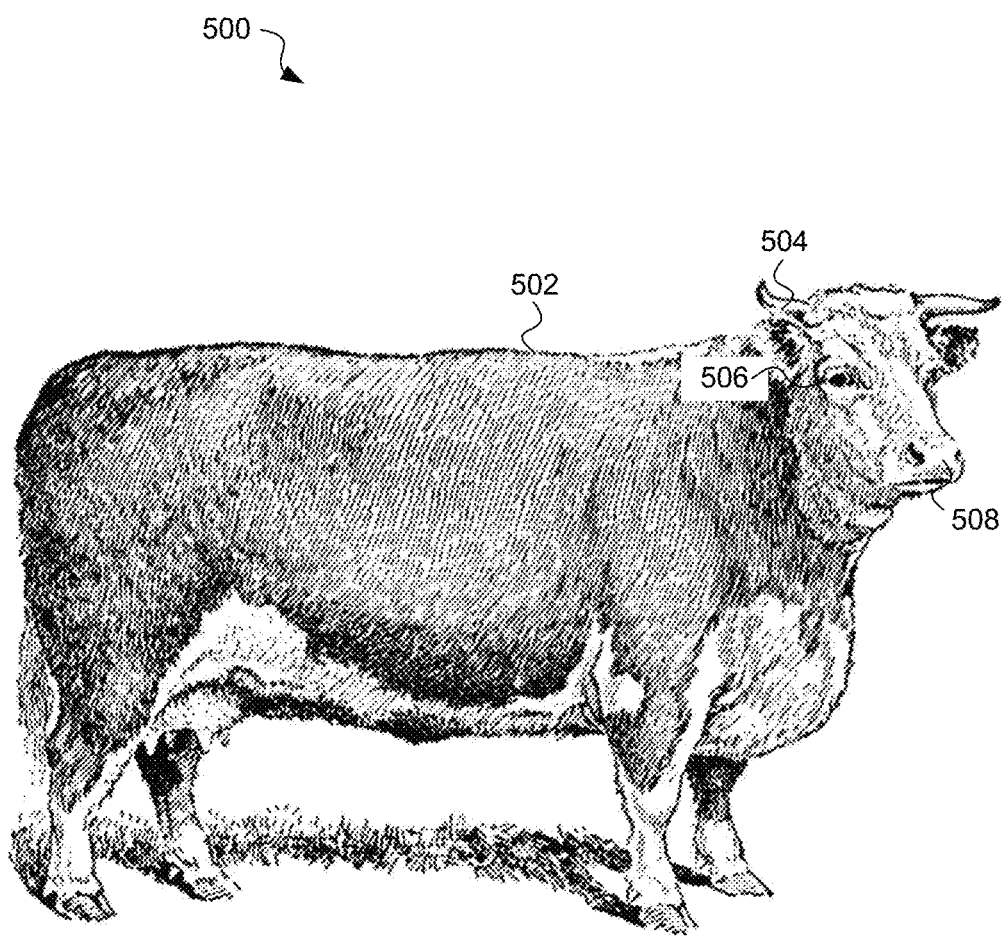
FIG. 5 is a diagram of an individual livestock with biometric markers for determining a biometric identity, according to an embodiment.

FIG. 3 is a flow chart showing a computer method 300 for livestock tracking and biometric identification, according to an embodiment which includes, at step 302, receiving, into a computer 106, 202, a first digital video or sequence of digital photographic frames from one or more digital image capture devices 104a, 104b, 104c, 104d, 104e. The digital image capture devices 104a, 104b, 104c, 104d, 104e may be referred to, collectively or individually, as 104 herein. The first digital video or sequence of digital photographic frames may include a plurality of livestock locations 102. Proceeding to step 304, a digital identity is assigned to each livestock individual in the pen. In step 308, locations of the livestock individuals are tracked as the livestock mill about. Referring to FIGS. 3 and 5, the method 300 may further include, at step 310, receiving a second digital video or digital photographic frame 500 including at least a portion of a biometric identification area 504, 506, 508 of an individual livestock body 502. A biometric deep sort is performed in step 312 to produce at least a portion of an individual livestock biometric identity. Proceeding to step 314, the individual livestock biometric identity is associated with a corresponding livestock digital identity. Step 314 may, for example, include associating the biometric and digital identities in a look up table, database, or other logical construct saved onto a non-transitory computer readable medium.

Figure 4:
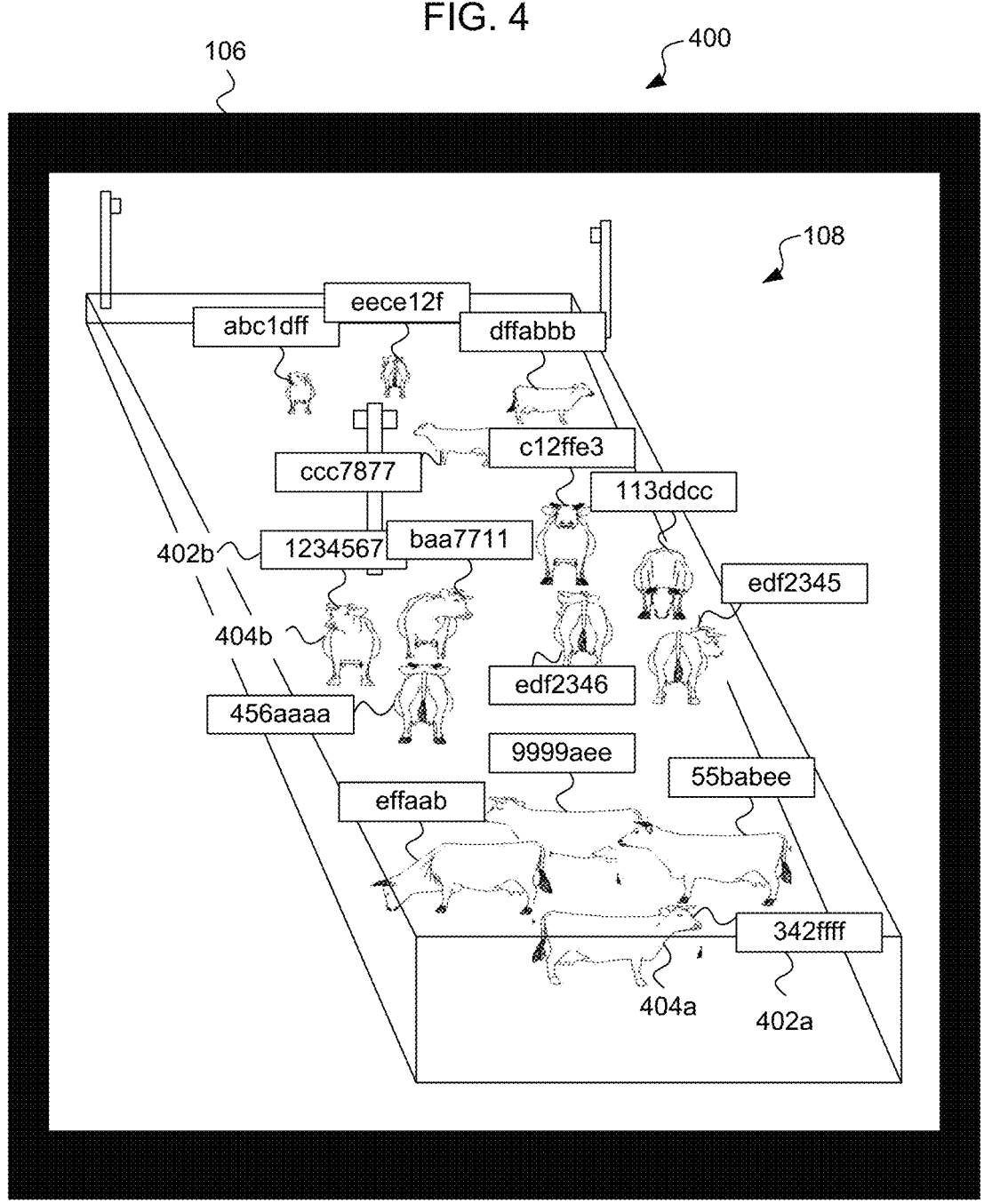
FIG. 4 is a diagram of information including livestock milling about with respective electronic identities output to an electronic display, according to an embodiment.

Referring to FIGS. 3 and 4, the method 300 may further include, in step 306, displaying a labeled image 400 on an electronic display 108, the labeled image including the current digital identities 402 corresponding each livestock individual.

According to an embodiment, tracking locations of the livestock individuals as the livestock mill about, in step 308, is performed using a Kalman filter. According to embodiments, tracking the locations of the livestock individuals may employ at least some parts of simultaneous localization and mapping (SLAM) which uses the Kalman filter. SLAM is usually used in robotics so the robot knows where in the environment it is located based on a few measurements.

In standard SLAM, the robot sends some lasers or pings in the environment to figure out where it is, based on a few reference points. In the present embodiment, if one uses multiple poles, each supporting a digital camera or video device, the pole locations serve as reference points from which the computer method, and specifically step 308, obtains measurements of the location and velocity of each detected class. In this case, the detected class is "livestock". With measurements from one or many poles, step 308 includes calculating a probability that a particular detected livestock individual is the same detected livestock individual from a previous few frames. The more poles there are, the more accurate the measurements will be for both tracking and identification.

Referring to FIG. 5, receiving, in step 310, the second digital video or digital photographic frame including at least a portion of a biometric identification area of an individual livestock body may include receiving a plurality of frames. According to an embodiment, performing the biometric deep sort further includes operating a Harris filter to locate livestock biometric markers. The Harris filter identifies corners in the frame, the corners being associated with the biometric markers. Performing the biometric deep sort in step 312 may include identifying, on a grid, relative locations of individual livestock biometric markers and storing the grid locations in an individual livestock biometric identity record in a livestock population model.

The individual livestock biometric markers include at least two of a corner of an eye, a corner formed by a horn, a corner formed by an ear, a snout corner, a hide color corner, a hoof corner, and/or a tail corner. Identifying individual biometric markers may include assigning classes of livestock body surface features and performing a semantic segmentation to classify each pixel as belonging to a livestock body surface feature. Assigning classes of livestock body surface features may include assigning livestock eye, livestock horn, livestock ear, livestock snout, livestock hide color patterns, livestock hoof, and/or livestock ear classes. Assigning classes of livestock body surface features may include assigning livestock eye corners and assigning livestock snout corners. Assigning classes of livestock body surface features may include assigning contrasting locations of skin and/or fur coloration. To perform identification, the computer method includes receiving a high resolution snapshot at a given time at which all heads, eyes, and snouts, are detected. Step 312 may include computing all face geometries. In step 314, the computer method 300 may include performing a probability computation against the database to get the most likely candidate electronic IDs corresponding to the biometric IDs. If a good candidate is obtained, the ID of that candidate may be assigned to the data recorded for the aforementioned detection. If multiple candidates are obtained, the multiple candidates, as well as secondary candidates, may be set to be reviewed during subsequent algorithm improvement iterations.

The first digital video or sequence of digital photographic frames received in step 302 may include a wider angle view including a plurality of livestock in the frame, compared to the second digital video or sequence of digital photographic frames includes a narrower angle view that includes less than all of the plurality of livestock in the frame. The narrower angle view may primarily include at least a portion of an individual livestock. In an embodiment, the narrower angle view consists essentially of the biometric identification area (e.g., see FIG. 5, 504, 506, 508) of the individual livestock's body 502.

The computer method 300 may further include receiving a third digital video or sequence of digital photographic frames including plurality of livestock locations in the pen as the livestock mill about, the plurality of livestock having corresponding digital identities and at least a portion of the plurality of livestock having been assigned a biometric identity. The individual livestock may be tracked (see step 308) as the livestock mill about, the individual livestock nominally being assigned livestock digital identities. The computer method 300 may further include receiving the second digital video or digital photographic frame corresponding to one of the individual livestock and including at least a portion of the biometric identification area of the individual livestock body, performing, in step 316, a second biometric identification of the individual livestock; and, in step 318, verifying that the tracked individual livestock is the individual livestock associated with the current livestock digital identity.

According to an embodiment, the computer method 300 may include tracking the individual livestock as the livestock mill about in step 308, the individual livestock nominally being assigned livestock digital identities, receiving the second digital video or digital photographic frame corresponding to one of the individual livestock and including at least a portion of the biometric identification area of the individual livestock body (see step 310), and performing biometric identification of the individual livestock.

The computer method 300 may include determining the individual livestock does not match a biometric identity of an individual livestock. If an individual livestock has not been biometrically identified, the computer method 300 may include performing the biometric deep sort (see step 312) to produce at least a portion of an individual livestock biometric identity, and (referring to step 314), associating the individual livestock biometric identity with the corresponding livestock digital identity. This may be used to gradually match individual livestock digital identities to individual livestock biometric identities after beginning tracking the livestock as the livestock mill about.

Improvement of the biometric identity may be obtained by determining that the biometric identity includes biometric markers not previously included in the biometric identity of the individual livestock (not shown) and augmenting the biometric identity with the additional biometric markers.

Figure 6:
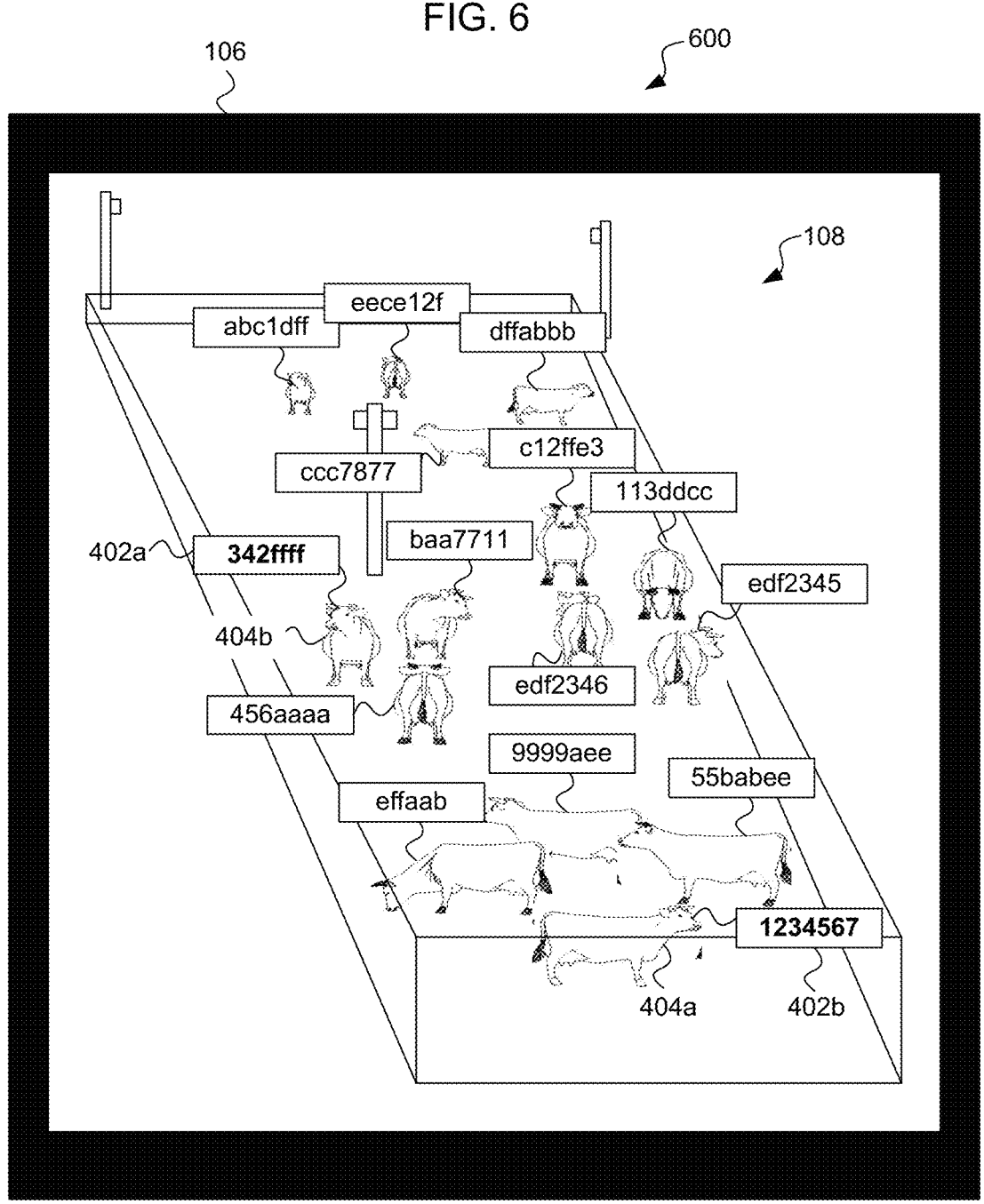
FIG. 6 is a diagram showing an electronic display where an electronic identity is adjusted to correspond to a biometric identity, according to an embodiment.

As may be appreciated with reference to FIG. 6, the individual livestock may occasionally be partially or completely obscured as the livestock mill about. This may cause the image processing software to, on occasion, lose certainty as to correct digital identities, thereby causing a reduction of correspondence between current digital identities and biometric identities of the livestock. To overcome this, the computer method may include periodically repeating biometric identification and, as appropriate, updating the digital identity. The computer method 300 may include determining that the tracked individual livestock 404a is an individual livestock associated with a different individual livestock digital identity 402b than an incorrect livestock digital identity 402a currently assigned to the first individual livestock 404a. The method 300 may then include, in step 318, assigning the correct individual livestock digital identity to the individual livestock. For example, comparing FIG. 4 to FIG. 6, see that individual livestock 404a, was incorrectly associated with digital identity 402a "342ffff". Upon the biometric deep sort, the individual livestock 404a, was found to have been assigned the digital identity associated with a different livestock 404b. Step 318 may include assigning the correct livestock digital identity 402b "1234567" previously associated with a different individual livestock 404b than the individual livestock 404a. Step 318 may include assigning the incorrect livestock digital identity 402a "342ffff" previously associated with the first individual livestock 404a to a second individual livestock 404b.

The livestock may be cows and/or steers. In other embodiments, the livestock may include sheep or goats.

Figure 7:
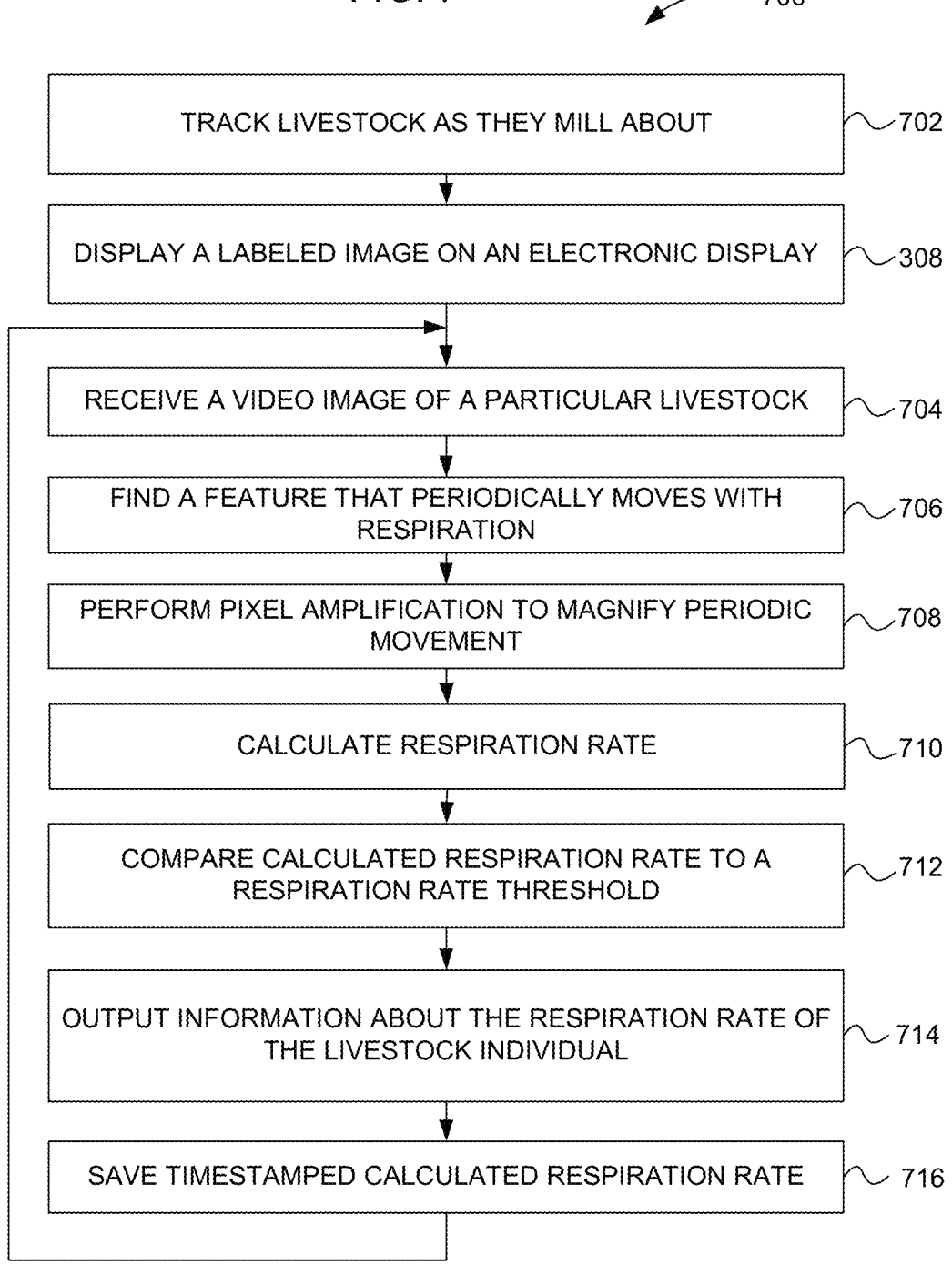
FIG. 7 is a flow chart showing a computer method for detecting respiration compromise in livestock, according to an embodiment.

FIG. 7 is a flowchart showing a computer method 700 for detecting respiratory compromise in livestock, according to an embodiment. Step 702 includes receiving a video stream including images of one or more livestock. In step 704, a digital identity of a livestock individual is determined from the video stream images. Step 706 includes finding, in frames of the video stream, an edge of the livestock individual that exhibits respiratory motion. Step 708 includes performing pixel amplification at the edge to amplify the respiratory motion. In step 710 a respiration rate of the livestock individual is determined from a sequence of the amplified edge pixels. In step 714, information about the respiration rate of the livestock individual is displayed on an electronic display.

Displaying information about the respiration rate of the livestock individual on an electronic display in step 714 may include displaying a notice that an individual livestock has a respiration rate that meets a threshold respiration rate indicative of respiratory distress. Displaying information about the respiration rate of the livestock individual on an electronic display in step 714 may include displaying an image of the individual livestock exhibiting a respiration rate that meets a threshold respiration rate indicative of respiratory distress. Displaying information about the respiration rate of the livestock individual on an electronic display in step 714 may include displaying an image of the one or more livestock as they mill about with the imaged of the individual livestock exhibiting a respiration rate highlighted. In this way, an individual livestock exhibiting respiratory distress, the cause of which may include communicable disease, may be quickly identified and removed from the population.

The computer method 700 may further include step 716, storing the determined respiration rate in a database including previously determined respiration rates of the livestock individual. In step 712, the determined respiration rate of the livestock individual may be compared to previously determined respiration rates of the first livestock individual. Step 712 may include determining if the determined respiration rate is different than the previously determined respiration rates. In step 714, the information corresponding to the respiration rate of the first livestock individual may be physically output.

Figure 8:
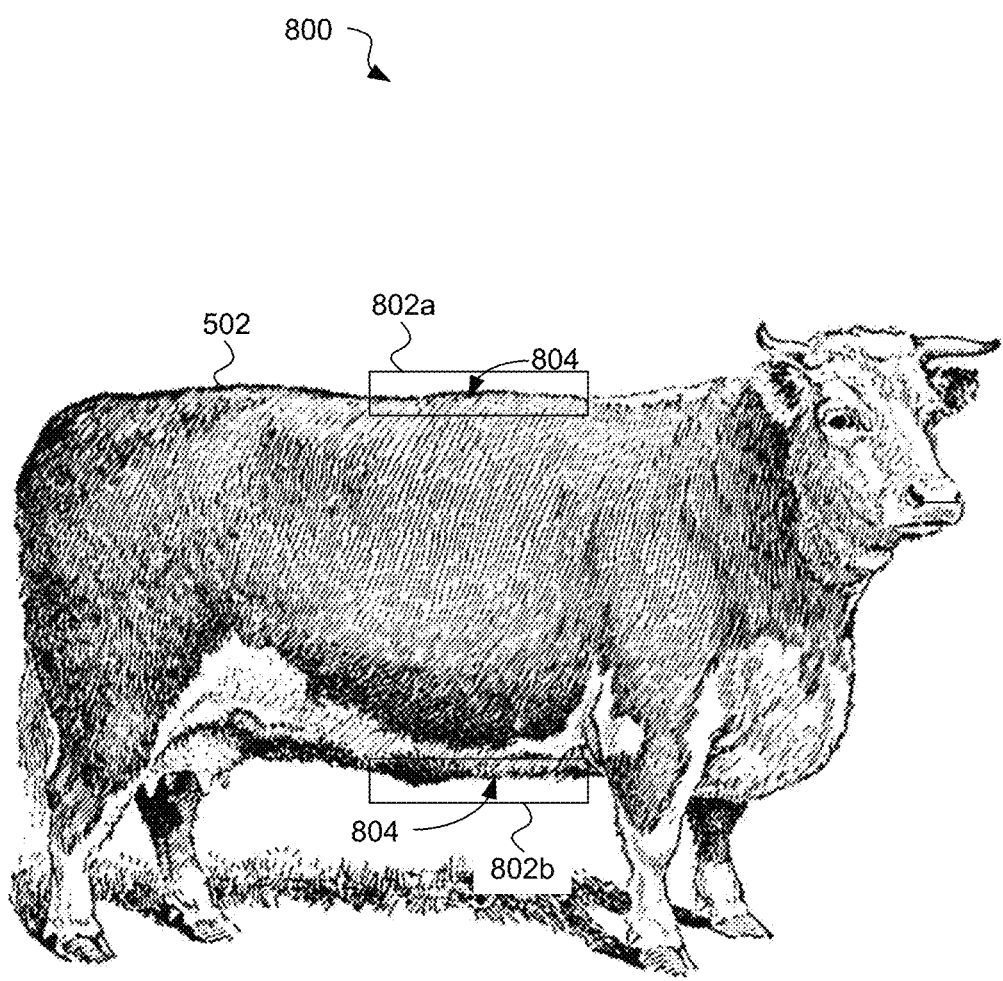
FIG. 8 is a diagram showing a livestock individual with a feature that exhibits periodic movement with respiration, according to an embodiment.

FIG. 8 is a diagram showing a feature of a livestock individual 502 that exhibits periodic movement with respiration. Referring to FIG. 7 in view of FIG. 8, finding the feature 804 that periodically moves with respiration, in step 706, may include producing a zoomed image 802a or 802b comprising a portion of the livestock individual 502. Finding the feature that periodically moves with respiration in step 706 may include, for example, finding a portion 802a on the back of the livestock individual 502, the belly 802b of the livestock individual, or other feature, depending on the posture (standing or laying) and orientation of the livestock to the camera 104 that captures the stream of images.

Performing pixel amplification at the edge to amplify the respiratory motion in step 708 may be performed using a Laplacian Pyramid. Using the Laplacian Pyramid may include creating negatives of each image at various resolutions and performing image addition with the original image on a frame-to-frame basis.

Performing pixel amplification at the edge to amplify the respiratory motion in step 708 may further include removing high frequency noise from an image addition frame sequence using a maximally flat magnitude filter within a passband corresponding to livestock respiration rate range. In an embodiment, the maximally flat magnitude filter within the passband comprises a Butterworth filter. In other embodiments, the maximally flat magnitude filter within the passband may include a Chebyshev filter or an elliptical filter.

In step 708, performing pixel amplification may include performing a Laplacian Pyramid and applying a Butterworth filter to form a video stream image traversing more pixels than not performing pixel amplification. In step 710, determining the respiration rate may include performing image analysis on one or more pixel-amplified video frame sequences. Additionally or alternatively, determining respiration rate in step 710 may include obtaining at least three video clips of pixel-amplified intervals and applying a filter to ensure the determined respiration rate is representative of an actual respiration rate of the livestock individual.

FIG. 9 is a diagram 900 showing a sequence of video frames 904, 906, 908, 910, including the feature 804 exhibiting pixel-amplified periodic movement, according to an embodiment. Referring to FIG. 7 in view of FIG. 9, performing pixel amplification at the feature 804 to amplify the periodic movement in step 708 may be performed using a Laplacian Pyramid. Using the Laplacian Pyramid may include creating negatives of each image at various resolutions and performing image addition with the original image on a frame-to-frame basis.

Performing pixel amplification at the feature 804 to magnify periodic movement in step 708 may include removing high frequency noise from an image addition frame sequence using a maximally flat magnitude filter within a passband corresponding to livestock respiration rate range. In an embodiment, the maximally flat magnitude filter within the passband comprises a Butterworth filter. In other embodiments, the maximally flat magnitude filter within the passband may include a Chebyshev filter or an elliptical filter. Performing pixel amplification in step 708 may include performing a Laplacian Pyramid and applying a Butterworth filter to form a video stream with greater dynamic range than a video stream where pixel amplification was not performed.

In step 710, calculating the respiration rate may include performing image analysis on one or more pixel-amplified video frame sequences. Determining respiration rate in step 710 may include obtaining at least three video clips of pixel-amplified intervals and applying a filter to ensure the calculated respiration rate is representative of an actual real time respiration rate of the livestock individual. Applying the filter to ensure the calculated respiration rate is representative of an actual respiration rate of the livestock individual may include applying a voting algorithm or performing respiration rate averaging.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A computer method for detecting respiratory compromise in livestock, comprising:
   receiving a video stream including images of one or more livestock;
   determining, from the video stream images, a digital identity of a livestock individual;
   finding, in frames of the video stream, an edge of the livestock individual that exhibits respiratory motion;
   performing pixel amplification at the edge to amplify the respiratory motion;
   determining a respiration rate of the livestock individual from a sequence of the amplified edge pixels; and
   displaying information about the respiration rate of the livestock individual on an electronic display.

2. The computer method for detecting respiratory compromise in livestock of claim 1, wherein displaying information about the respiration rate of the livestock individual on an electronic display includes displaying a notice that an individual livestock has a respiration rate that meets a threshold respiration rate indicative of respiratory distress.

3. The computer method for detecting respiratory compromise in livestock of claim 1, wherein displaying information about the respiration rate of the livestock individual on an electronic display includes displaying an image of the individual livestock exhibiting a respiration rate that meets a threshold respiration rate indicative of respiratory distress.

4. The computer method for detecting respiratory compromise in livestock of claim 1, wherein displaying information about the respiration rate of the livestock individual on an electronic display includes displaying an image of the one or more livestock as they mill about with the image of the individual livestock exhibiting a respiration rate highlighted.

5. The computer method for detecting respiratory compromise in livestock of claim 1, further comprising:
   storing the determined respiration rate in a database including previously determined respiration rates of the livestock individual.

6. The computer method for detecting respiratory compromise in livestock of claim 1, further comprising:
   comparing the determined respiration rate of the livestock individual to previously determined respiration rates of the first livestock individual; and
   determining if the determined respiration rate is different than the previously determined respiration rates.

7. The computer method for detecting respiratory compromise in livestock of claim 1, wherein performing pixel amplification at the edge to amplify the respiratory motion is performed using a Laplacian Pyramid.

8. The computer method for detecting respiratory compromise in livestock of claim 7, wherein using the Laplacian Pyramid includes:
   creating negatives of each image at various resolutions; and
   performing image addition with the original image on a frame-to-frame basis.

9. The computer method for detecting respiratory compromise in livestock of claim 1, wherein performing pixel amplification at the edge to amplify the respiratory motion further comprises:
   removing high frequency noise from an image addition frame sequence using a maximally flat magnitude filter within a passband corresponding to livestock respiration rate range.

10. The computer method for detecting respiratory compromise in livestock of claim 1, wherein performing pixel amplification includes performing a Laplacian Pyramid and applying a Butterworth filter to form a processed video stream traversing more pixels than not performing pixel amplification.

11. The computer method for detecting respiratory compromise in livestock of claim 1, wherein determining the respiration rate includes performing image analysis on one or more pixel-amplified video frame sequences.

12. The computer method for detecting respiratory compromise in livestock of claim 1, wherein determining respiration rate includes:
   obtaining at least three video clips of pixel-amplified intervals; and
   applying a filter to ensure the determined respiration rate is representative of an actual respiration rate of the livestock individual.

13. The computer method for detecting respiratory compromise in livestock of claim 12, wherein applying the filter to ensure the determined respiration rate is representative of an actual respiration rate of the livestock individual includes applying a voting algorithm or performing respiration rate averaging.

* * * * *